United States Patent [19]

Kippel et al.

[11] 4,133,656
[45] Jan. 9, 1979

[54] BACTERIA FILTERS WITH TRANSPARENT HOUSINGS

[75] Inventors: Edward A. Kippel, Suffern, N.Y.; Paul O. Huston, Montville, N.J.

[73] Assignee: Becton, Dickinson and Company, East Rutherford, N.J.

[21] Appl. No.: 765,111

[22] Filed: Feb. 2, 1977

Related U.S. Application Data

[62] Division of Ser. No. 669,622, Mar. 23, 1976, abandoned.

[51] Int. Cl.$^2$ ............................................. B01D 46/00
[52] U.S. Cl. ........................................ 55/274; 128/188
[58] Field of Search .................... 55/274, 360; 128/188

[56] References Cited

U.S. PATENT DOCUMENTS

| | | | |
|---|---|---|---|
| 1,574,422 | 2/1926 | Feind | 55/360 |
| 2,990,032 | 6/1961 | Sandvig | 55/274 |
| 3,556,097 | 1/1971 | Wallace | 128/188 |
| 3,721,238 | 3/1973 | Wise et al. | 128/188 |

FOREIGN PATENT DOCUMENTS

247865  2/1926  United Kingdom ...................... 55/274

*Primary Examiner*—Bernard Nozick
*Attorney, Agent, or Firm*—Kane, Dalsimer, Kane, Sullivan & Kurucz

[57] ABSTRACT

A bacteria filter for use in anesthesiology and respiratory care systems to filter fluid flow at a desired point in a system. The filter includes an enlarged nonconductive, transparent tubular housing having a passageway therethrough and tapering at one end to a reduced tip. A conductive connector is mounted to the reduced tip and a conductive end cap is affixed to the end of the housing distal from the reduced tip. The end cap has an opening therethrough terminating in a projecting connector. A filter element is retained in the housing and a conductive portion extends between the end cap and the conductive connector to provide a conductive pathway from end to end of the filter. The connector and the projecting end cap are adapted to be mounted within a fluid flow system to permit fluid communication with the interior of the housing so that fluid flow through the system passes in one end of the housing, through the filter element and out the other end of the housing.

1 Claim, 11 Drawing Figures

BACTERIA FILTERS WITH TRANSPARENT HOUSINGS

This is a division of application Ser. No. 669,622, filed Mar. 23, 1976, now abandoned.

BACKGROUND OF THE INVENTION

In anesthesia and respiratory care breathing systems, it has been found that it is desirable at times to filter gases or fluids prior to their introduction to the patient. An example of a system of this type is disclosed in U.S. Pat. No. 3,556,097.

On occasion, certain problems occur during the filtering process which require independent consideration. For example in handling certain types of gases an electrical problem occurs which makes it desirable to have a filter which is of a conductive material to alleviate the problems. However, with known conductive materials within a reasonable cost range, there is no known material which is transparent in nature. This combination leads to an additional concern. During the handling of the gases, particularly gases which have been passed through absorbers and vaporizers, during the filtering process a certain amount of condensation occurs as the gas passes through the filter medium. The condensation on a continuous basis results in a condensate build-up which eventually would clog the filter. With conductive housings of a non-transparent nature it is impossible to observe the condensate build-up within the filter and, consequently, with known systems it is necessary to replace the filter at periodic intervals as a safety measure without actually knowing the extent of condensate build-up.

Carrying this concern one step further, with the filters presently in use there is no structure which provides for removal of condensate build-up were it possible to observe this development. The filters could be used until they completely fill beyond an acceptable condensate level and then they would have to be removed from the system.

Another consideration of the known filters for the environment under consideration is that they are generally designed to interconnect with a system of a predetermined arrangement. It would be extremely advantageous to provide a filter which is adaptable for connection with a variety of different types of breathing systems without altering the physical structure of the filter itself.

Finally, above all, it is imperative that the filter be of low cost disposable materials so as to be compatible with general systems presently in use which are primarily designed for single use. On the other hand, the filter should be versatile enough so that the condensate build-up can be removed during the single use without the necessity of having to use a multiple of filters for an individual patient.

SUMMARY OF THE INVENTION

With the above background in mind, it is among the primary objectives of the present invention to provide a disposable filter and is designed for interconnection with a variety of well-known anesthesiology and respiratory care systems. The filter is adapted to receive fluid flow therethrough in either axial direction, contains a conductive path from end to end to alleviate electrical dangers, includes a transparent housing to permit the observation of condensate build-up within the filter during use, and contains a valve mechanism on the filter to drain condensate which has built up beyond a desirable level within the filter during use thereby alleviating the necessity of use of multiple filters for a single patient. The provision of a conductive path along with the transparent housing to permit observation of condensate build-up and the valve to drain excessive condensate combine to alleviate well known patient safety hazards.

In summary, a bacteria filter is provided for use in anesthesiology and respiratory care systems to filter fluid flow at a desired point in the system. The filter includes an enlarged non-conductive, transparent tubular housing having a passageway therethrough and tapering at one end to a reduced tip. A conductive connector is mounted to the reduced tip and a conductive end cap is affixed to the end of the housing distal from the reduced tip. The end cap has an opening therethrough terminating in a projecting connector. A filter element is retained in the housing and a conductive portion extends between the end cap and the conductive connector to provide a conductive pathway from end to end of the filter. The connector and the projecting connector are adapted to be mounted within a fluid flow system to permit fluid communication with the interior of the housing so that fluid flow through the system passes in one end of the housing, through the filter element and out the other end.

With the above objectives, among others, in mind, reference is had to the attached drawings.

DESCRIPTION OF THE PREFERRED EMBODIMENTS

Figure 1:
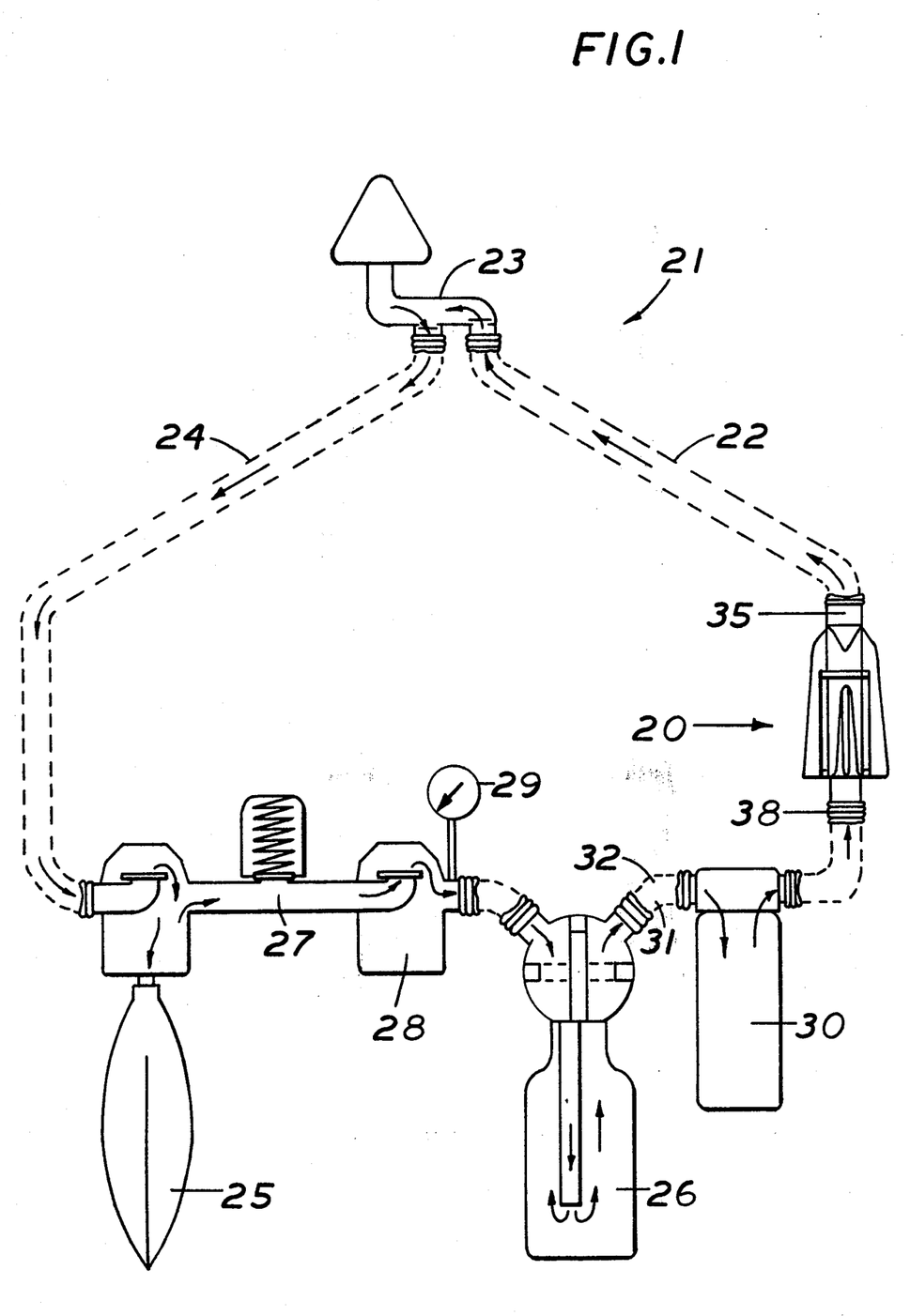
FIG. 1 is a schematic view of the filter of the invention in operable position within a representative anesthesia breathing circuit.
Figure 2:
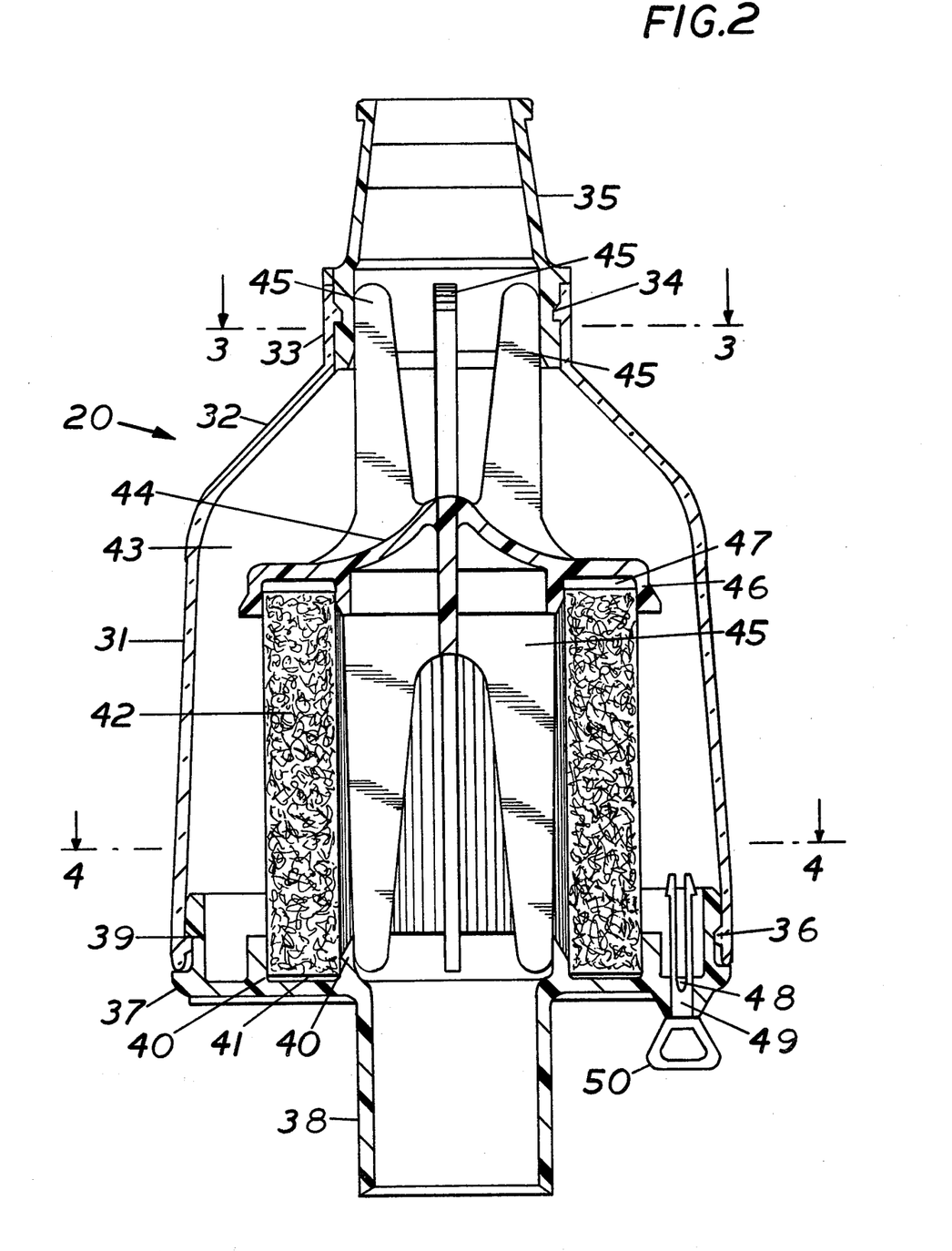
FIG. 2 is a sectional elevation view of the filter of the invention.
Figure 3:
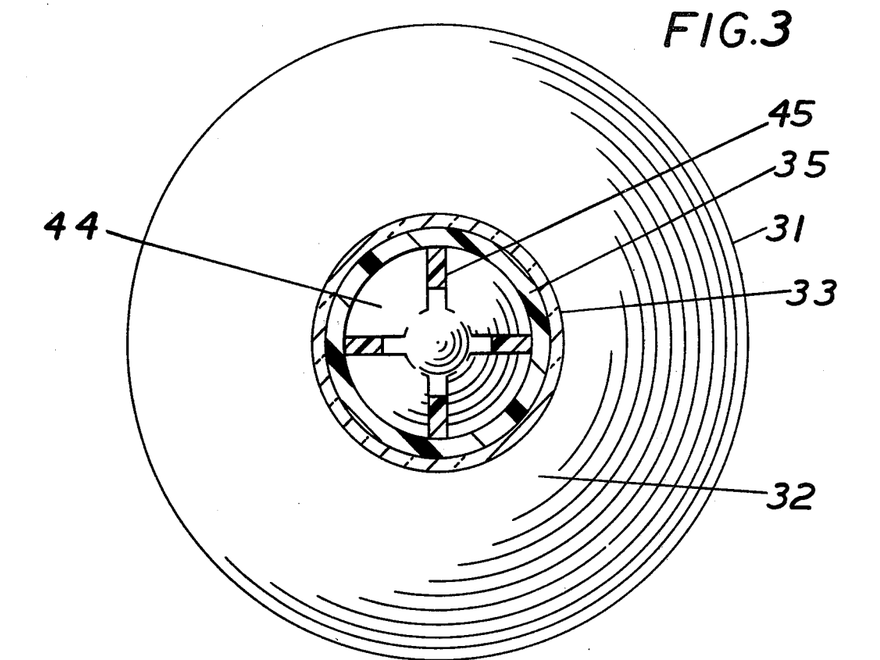
FIG. 3 is a cross-sectional view of the filter taken along the plane of line 3—3 of FIG. 2.
Figure 4:
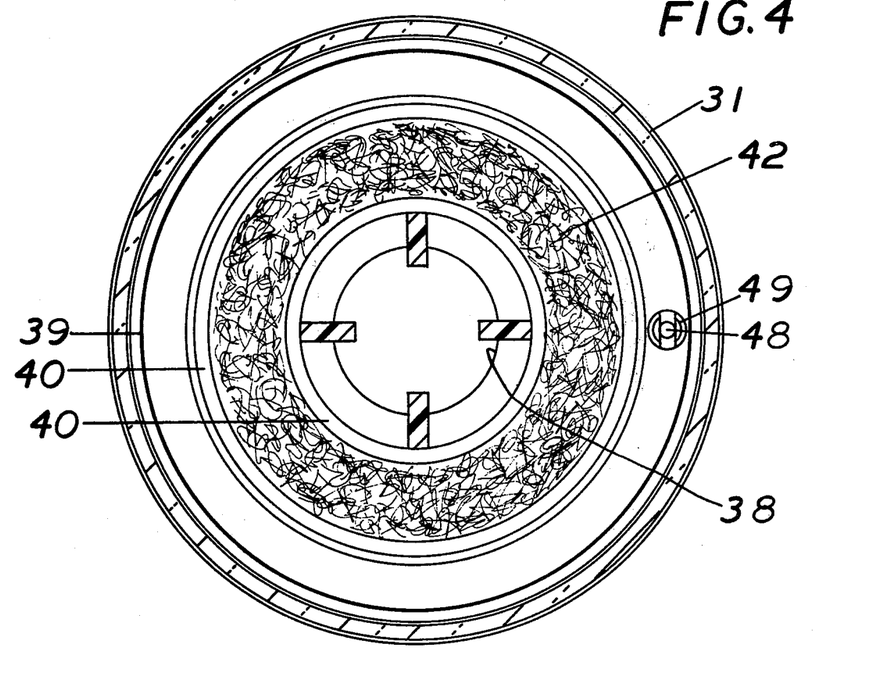
FIG. 4 is a cross-sectional view of the filter taken along the plane of line 4—4 of FIG. 2.

Filter 20 is depicted independently in FIGS. 2, 3 and 4 and is shown in cooperation within a conventional well known type of anesthesia breathing circuit 21 in FIG. 1. Filter 20 is adapted to pass flow therethrough in either direction and is open at both ends. One end of filter 20 is connected to a corrugated conduit 22 which passes directly to a patient breathing mechanism 23. The other end of filter 20 is connected in line to a source of gases for filtering prior to introduction to the patient. In a conventional apparatus as shown, the gases may originate in part from an exhalation conduit 24 passing from the breathing mechanism 23 and entering through a check valve into a breathing bag 25. The exhalation gases then pass from breathing bag 25 into an absorber apparatus 26 for absorption of liquid to enhance the gases for reception by the patient. Monitoring the passage from breathing bag 25 to absorber apparatus 26 are appropriate valve engaging apparatus such as pressure relief valve 27, exhalation check valve assembly 28, and pressure gauge 29. Appropriate conduit means are provided to guide the gases from the breathing bag to the absorber apparatus as monitored by valves and gauges as discussed above.

The gases exit absorber apparatus 26 and are passed to a vaporizer 30 through an appropriate conduit 31. An inlet 32 is provided along conduit 31 for introduction of fresh gas to be mixed with the gas from the absorber apparatus 26. The mixture is then vaporized in a well known manner in vaporizer 30 and is passed from the vaporizer 30 to the filter 20 for filtering prior to introduction through conduit 22 and breathing device 23 to the patient.

Turning to consideration of the filter 20, an enlarged tubular housing 31 is provided with openings at both ends. At one end the housing tapers at portion 32 until it terminates in an annular reduced tip 33. An internal rib extends inwardly from the inner surface of reduced tip 33 for interlocking with a conductive connector 35.

The other end of enlarged tubular housing 31 contains an annular rib 36 adjacent its end for facilitating interengagement with a conductive end cap 37. A projecting connector portion 38 which is tubular in configuration and open at both ends extends from a central location from end cap 37 away from housing 31. End cap 37 has a plurality of concentric ribs extending inwardly of housing 31 with the outer rib 39 having appropriate detent to interengage with rib 36 of housing 31 and thereby lock the end cap to the housing. The inner two concentric ribs 40 form an annular recess 41 for reception of one end of a filter element 42. The filter element is hollow and cylindrical in configuration.

Housing 31 is of a transparent non-conductive material of plastic or other conventional material having the similar properties. In contrast, conductive connector 35 and end cap 37 including projecting connector 38 are of an electrically conductive material. Once again the material may be plastic or other well known conventional substance having similar properties.

Projection 38 and connector 35 need not be transparent in nature as long as enlarged housing 31 is transparent so that the interior chamber 43 thereof can be observed at all times during operation of the filter. Both ends of filter 20 are conductive in nature in the form of connector 35 and projecting connector 38 and in order to provide a conductive path throughout the entire length of filter 20, it is necessary to provide an intermediate portion of conductive material extending between connector 35 and connector 38. This may take the form of a strip of material along the length of housing 31 on the exterior surface thereof and interconnected at its ends with connector 35 and connector 38. The strip may be fastened to the outer surface of housing 31 by means of an adhesive or other conventional means. Alternatively, in the form depicted, the conductive portion can be a finned element 44 extending axially through the interior of housing 31 and interengaging with connector 35 and connector 38 at each respective end. The plurality of fins 45 on finned element 44 are spaced circumferentially apart so as to increase the contact points and assure a continuous conductive path from connector 38 through housing 31 to connector 35. Intermediate the ends of the finned element 44 is a circular tray 46 with an appropriate annular recess 47. Recess 47 is in alignment with recess 41 on the interior surface of end cap 37. The two recesses 47 and 41 receive opposed ends of hollow tubular filter element 42 and thereby mount the filter element within housing 31 for use.

Connector 35 has an outer surface configuration which facilitates its use as a male connector for introduction within an appropriate conduit of a breathing system. In contrast, connector 38 is provided with inner and outer surfaces so that it is adapted to receive a male connector element of a breathing system. In this manner, one end of the filter is formed as a male connector element and the other end of the filter is formed as a female connector element. Fluid flow can proceed in either direction through filter 20 and, accordingly, connectors 38 and 35 are interchangeable thereby adding to the versatility of filter 20 for interconnection within a breathing system.

The end wall of end cap 37 is also provided with an aperture 48 therethrough to provide communication between the exterior of the filter and the interior of chamber 43. Normally positioned in aperture 48 is a plug 49 which seals with the walls forming the aperture to prevent fluid flow into or out of the filter. When plug 49 is positioned within the aperture a gripping portion 50 extends rearwardly from end cap 37 and exteriorly of housing 31. Consequently, plug 49 can be removed from aperture 48 by grasping portion 50 and withdrawing the plug from the aperture. This opens a fluid access path to and from the interior of chamber 43 and filter housing 31.

In use, connector 38 is connected to a source of gases for introduction to a patient such as vaporizer 30 and connector 35 is connected to a conduit such as conduit 22 in FIG. 1 for introduction directly to a patient's breathing device. Gases then pass through the hollow interior of connector 35 into chamber 43 and through filter element 42. Once through filter element 42 it has access to connector 35 and introduction to the patient in filtered form. During the passage of gases through filter 20 an accumulation of condensate will occur within chamber 43. With housing 31 being of a transparent material the condensate build-up can be observed until it reaches an undesirable level. At that point, plug 49 can be removed to permit drainage of condensate. Thereafter the plug can be replaced and the filtering process can continue. Since the filter is of disposable material, once the single patient use is completed, the filter can be disposed of. A continuous conductive path exists from end to end in filter 20 through the interconnection of connectors 35 and 38 and portion 44. This alleviates the danger of electrical problems developing in the filter portion of the system.

For use as waterproof filter element 42, it has been found that Purolator Grade A filter paper treated with phenolic coating and G E Dry Film 104 waterproofing agent 0.4% as developed by the Aerospace Division of Purolator, Inc., Newbury Park, California, is satisfactory. Naturally, other available acceptable filter material having the desired properties would be equally acceptable.

In general for use in anesthesia and/or respiratory bacteria filtering environments, certain general criteria must be met. Accordingly, filter 20 satisfies the general criteria. The minimum particle size filtered should be on the order of 0.3 microns absolute with 99+% of filter efficiency. The filter is designed to handle a variety of gases such as 100% oxygen, cyclopropane/oxygen, nitrous-oxide/oxygen, ethyl-ether/oxygen, halothane (fluothane)/ oxygen, methoxyfluorane (penthrane)-/oxygen, air, carbon dioxide, water vapor-saturated at 97–105° F (approximately 44 gms/cubic meter), and other anesthetics and medications.

Filter 20 for use in the desired environment is adapted to handle gas flow rates of 0-100LPM and 0-4CFM. The operating pressure is 20–50 cm $H_2O$. The highest acceptable flow resistance is on the order of 2 cm $H_2O$ at 100LPM with an optimum flow resistance of 1 cm $H_2O$ at 100 LPM.

Filter 20 is designed for an acceptable shell life prior to use such as 3 to 5 years and for a single patient use of approximately 8 to 24 hours.

The unit is autoclavable and is capable of ethylene oxide sterilization (for example 120–135° F, 50% humidity, 24 hours).

Housing 31 of filter 20 is designed for an approximate maximum electrical resistance of 10,000 ohms which is not affected by anesthetics or medications.

Figure 5:
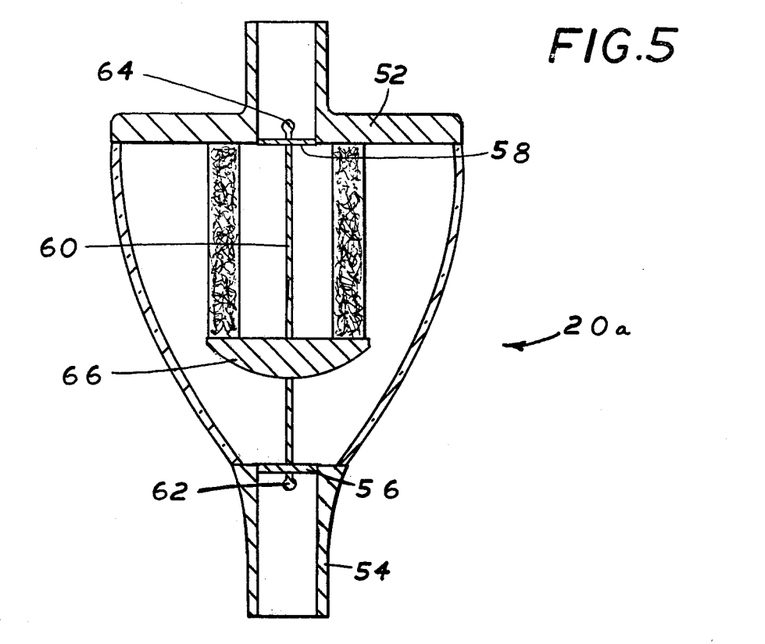
FIG. 5 is a cross sectional view of an alternative form of the filter of the invention.

The embodiment of FIGS. 1-4 which have been described in detail above is subject to many alternatives in design. For example, FIG. 5 shows a filter 20a which is similar in general configuration and design to filter 20 with the difference in structure residing in the nature of the conductive path between the end cap 52 and the conductive connector 54 at the opposite end. Web 56 of resilient material is provided with a central aperture adapted to be resiliently enlarged upon the application of sufficient force and then to return to its initial configuration upon relief of the force. A similar web 58 is provided in end cap 52. The webs are of conductive material and are designed to receive in snap-in fashion the enlarged knobs on the end of a central post 60 extending axially through the center of the filter. The post is also of conductive material and has a knob 62 at one end and a knob 64 on the other end with each knob adapted to snap into position within a corresponding web. Intermediate the ends of the post is a centrally located disc 66 of conductive material which is designed to engage with one end of the filter and cooperate with the inner surface of end cap 52 to hold the filter in position. Alternatively, the single post 60 can be in the form of two posts one extending from either side of the disc 66. The post provides the connection between end cap 52 and connector 54 thereby providing the end to end electrical connection for the structure.

Figure 6:
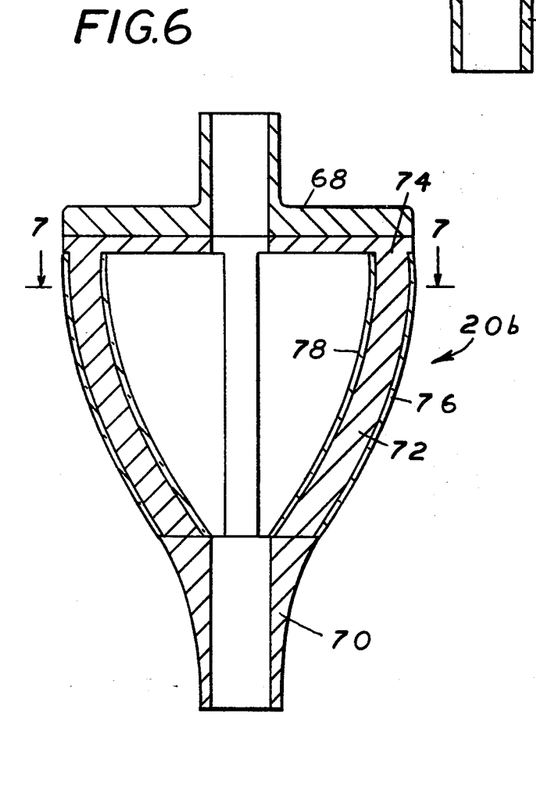
FIG. 6 is a cross sectional view of a second alternative form of the filter of the invention.
Figure 7:
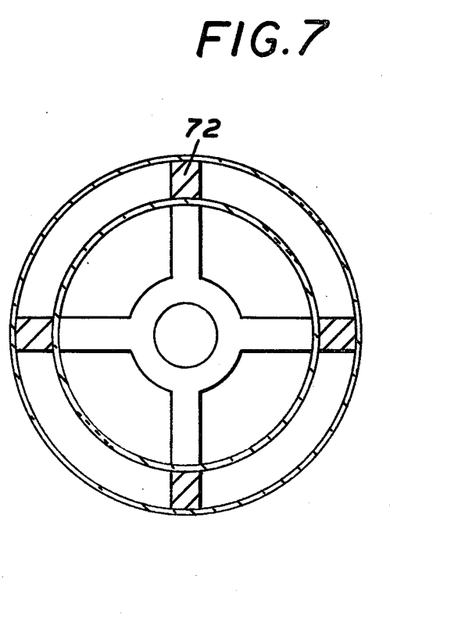
FIG. 7 is an end sectional view thereof taken along the plane of line 7—7 of FIG. 6.

A further alternative form is shown in FIGS. 6 and 7 as filter 20b. Once again the design and configuration of the filter is the same as in previously discussed embodiments with the difference residing in the form of the conductive path between the end cap 68 at one end and the conductor 70 at the other end. In this embodiment the conductive path is provided by a group of four spaced suspenders 72, the number of suspenders is a matter of choice, which are interconnected at one end by a circular ring 74 so as to form a basket like arrangement. One end of each suspender 72 engages with conductive end cap 68 through ring 74 and the other end of each suspender engages with the conductive connector 70. In this manner the end to end conductive path is provided. The suspenders are held in position by being contained within a double molded clear housing having an outer wall 76 and an inner wall 78.

Figure 8:
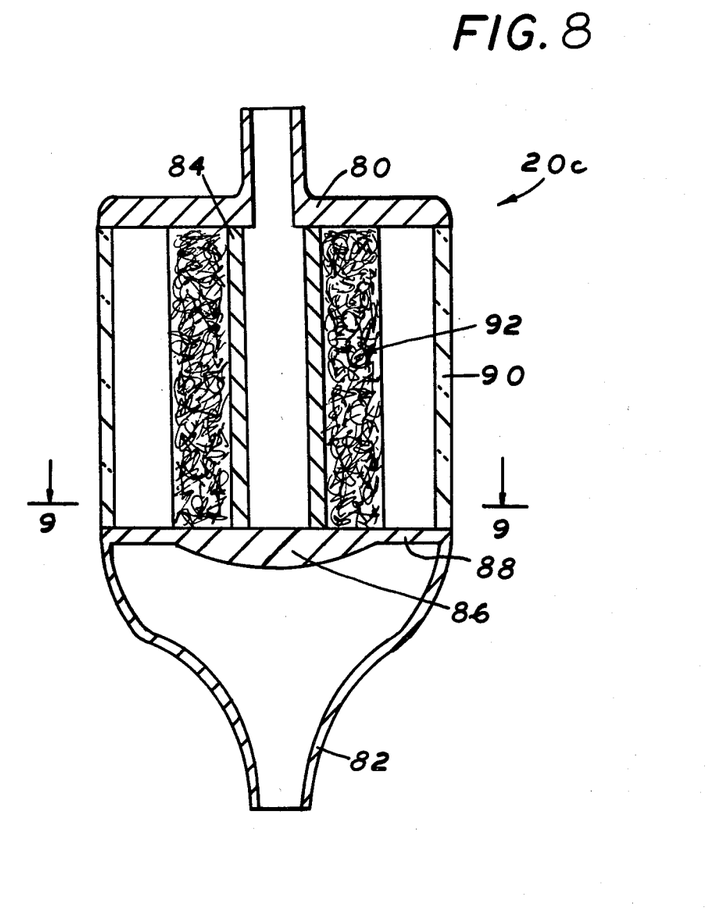
FIG. 8 is a cross sectional view of a third alternative form of the filter of the invention.
Figure 9:
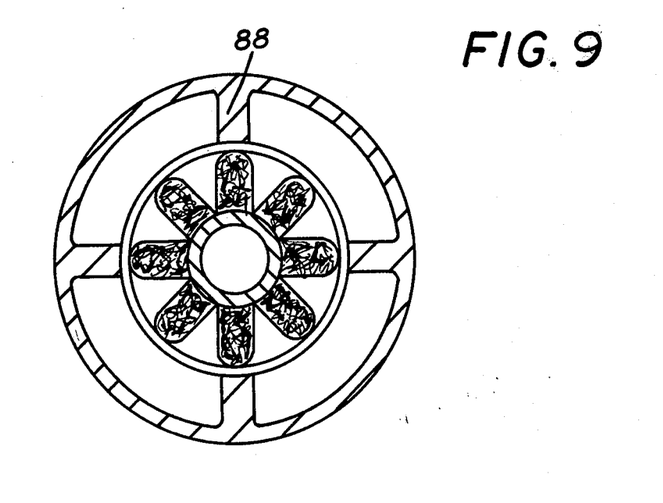
FIG. 9 is an end sectional view thereof taken along the plane of line 9—9 of FIG. 8.

FIGS. 8 and 9 show another alternative form of filter 20c which once again substantially the same as the previously discussed embodiments with the exception of the form of conductive path extending between end cap 80 and the reduced tip conductive connector portion 82 at the other end. In this form a centrally located porous conductive cylinder 84 is provided with one end in direct contact with the conductive end cap 80 and the other end in direct contact with a centrally located disc 86 of conductive material at its other end. The disc is supported and interconnected with a group of four angularly spaced spokes 88, the number of spokes is a matter of choice, which are in turn connected to the conductive end portion 82. With portions 80, 82, 84, 86 and 88 being conductive a full conductive pathway is provided from end to end of the filter while still maintaining the use of a clear housing 90. The central disc 86 cooperates with the inner surface of end cap 80 to retain a filter element 92 in fixed position within the housing.

Figure 10:
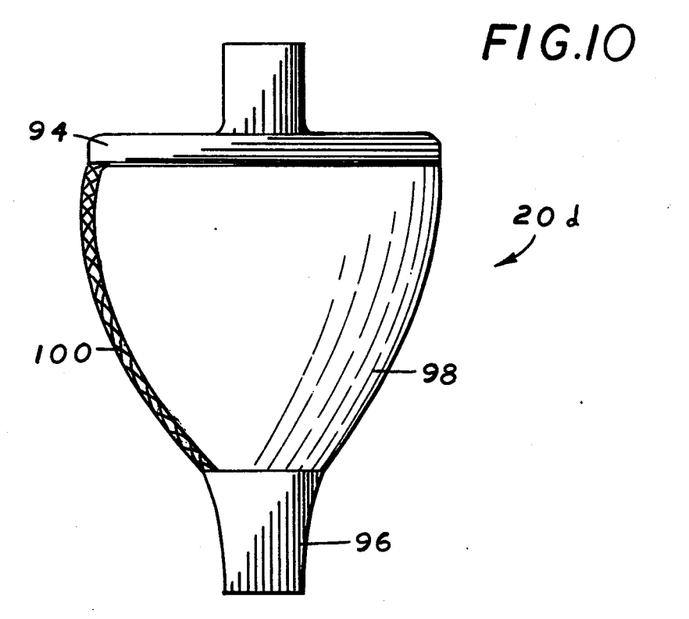
FIG. 10 is a plan view of a fourth alternative form of the filter of the invention.

A further embodiment of the filter is depicted as filter 20d in FIG. 10 of the drawings. In all respects the filter operates the same as in the previously discussed embodiments with the exception, once again, of the conductive path between the conductive end cap 94 and the opposing end conductive connector 96. In this form, adhered to the outer surface of the clear housing 98 is a strip 100 of conductive material. The strip is attached at one end to conductive connector 96 and at the other end to conductive end cap 94 thereby providing the end to end conductive path for the filter. The strip can be adhered to in any conventional fashion to the clear housing such as by an epoxy or it can be merely resting adjacent to or on the housing without any direct connection as long as it is connected to the end cap 94 at one end and the connector 96 at the other end.

Figure 11:
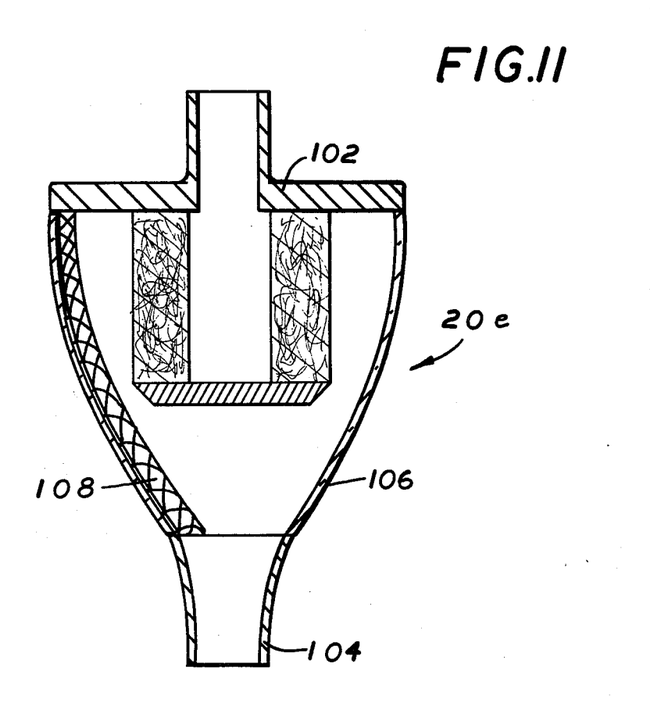
FIG. 11 is a cross sectional view of a fifth alternative form of the filter of the invention.

A final depicted form of filter 20e is depicted in FIG. 11 and is also similar in design to the previous embodiments with the exception of the design and positioning of the conductive path between one conductive end cap 102 and the other conductive end connector 104. A clear transparent housing 106 is employed and positioned inside of the housing is a conductive strip 108 which is closely positioned to the wall of the housing or adhered thereto by a conventional epoxy or by any other similar means as in the previously discussed embodiment. The strip 108 is connected at one end to conductive connector 104 and at the other end to conductive end cap 102 thereby providing the end to end continuous conductive path. As previously stated, the strip can be merely positioned adjacent to the inner wall of transparent housing 106 as depicted in FIG. 11 or can be adhered directly to the surface as shown with respect to the embodiment of FIG. 10.

It is also contemplated that the filter could be designed with similar conductive end connections and with the clear conductive housing that would be gold filled or contain a grafted conductive surface which would provide the end to end conductive path for the filter.

Thus the several aforenoted objects and advantages are most effective attained. Although several somewhat preferred embodiments have been disclosed and described in detail herein, it should be understood that this invention is in no sense limited thereby and its scope is to be determined by that of the appended claims.

We claim:

1. A bacteria filter for use in anesthesiology and resporatory air systems to filter fluid flow at a desired point in a system comprising:
   an enlarged electrically non-conductive, transparent tubular housing having a passageway therethrough and having at one end a reduced tip;
   an electrically conductive connector mounted to the reduced tip;
   an electrically conductive end cap affixed to the end of the housing distal from the reduced tip;
   the end cap having an opening therethrough terminating in a projecting end cap connector;
   a filter element mounted in the housing;
   an electrically conductive portion extending between the end cap and the electrically conductive connector to provide an electrically conductive pathway from end to end of the filter including the space occupied by the transparent housing;
   the connector and the projecting end cap connector being adapted to be mounted within a fluid flow system to permit fluid communication with the interior of the housing so that fluid flowing through the system passes in one end of the housing, through the filter element and out of the other end;
   the connector, the housing and the end cap being arranged in a series relationship with means between the connector and the projecting end cap providing a fluid flow from said system through one end of the housing, through the filter element and out of the other end and the electrically conductive portion being a conductive strip extending from end to end of the series relationship and being mounted entirely on the interconnected housing, connector, and end cap independent of external supporting structure; and
   the electrically conductive portion extending between the end cap and the electrically conductive connector being a conductive strip on the transparent interior surface of the housing, the strip covering a minimal portion of the circumferential area of the tubular housing so as to provide minimum interference with the visual observation of the interior of the housing while providing for an electrically conductive pathway from end to end of the filter.

* * * * *